United States Patent [19]
Bristol et al.

[11] Patent Number: 4,507,294
[45] Date of Patent: Mar. 26, 1985

[54] IMIDAZO[1,2-a]PYRAZINES

[75] Inventors: James A. Bristol, Ann Arbor, Mich.; Raymond G. Lovey, West Caldwell, N.J.

[73] Assignee: Schering Corp., Kenilworth, N.J.

[21] Appl. No.: 356,052

[22] Filed: Mar. 8, 1982

[51] Int. Cl.³ .................. C07D 413/04; A61K 270/00
[52] U.S. Cl. ..................................... 514/249; 544/117; 544/350; 544/354; 544/356; 514/227; 514/233
[58] Field of Search ............... 544/350, 117; 424/251, 424/248.4

[56] References Cited

U.S. PATENT DOCUMENTS

| | | | |
|---|---|---|---|
| 4,233,301 | 11/1980 | Baldwin et al. | 544/350 |
| 4,242,344 | 12/1980 | Lumma | 544/350 |

OTHER PUBLICATIONS

Abignente, E. et al., Il Farmaco-Ed. Sc. vol. 36, pp. 61-80, "Research on Heterocyclic Cpds."

Primary Examiner—Donald G. Daus
Assistant Examiner—S. A. Gibson
Attorney, Agent, or Firm—Gerald S. Rosen

[57] ABSTRACT

There are disclosed herein certain substituted imidazo[1,2-a]pyrazine compounds which are useful in the treatment of peptic ulcer diseases.

25 Claims, No Drawings

IMIDAZO[1,2-a]PYRAZINES

SUMMARY OF THE INVENTION

This invention relates to certain substituted imidazo[1,2-a]pyrazine compounds, pharmaceutical compositions thereof, novel processes and intermediates for making said compounds, and methods of treating peptic ulcer disease utilizing said compounds.

More particularly, this invention relates to imidazo[1,2-a]pyrazine compounds represented by the following structural formulas I and II:

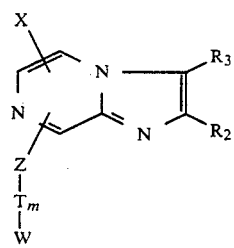

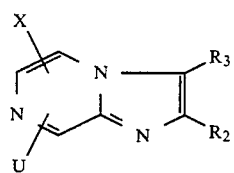

the 5,6,7,8-tetrahydro, 2,3-dihydro and perhydro derivatives thereof, and pharmaceutically acceptable salts thereof, wherein:

U represents

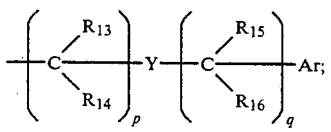

$R_2$ and $R_3$ each independently represents hydrogen, lower alkyl, trifluoromethyl, B—$CF_3$, Ar, B—Ar, halogen, B-halogen, —$OR_7$, B—$OR_8$, B—$SR_6$, —$S(O)_n$—$R_7$, B—$S(O)_n$-lower alkyl, (wherein n is zero, one or two),

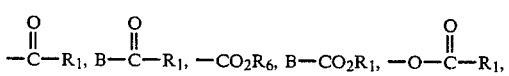

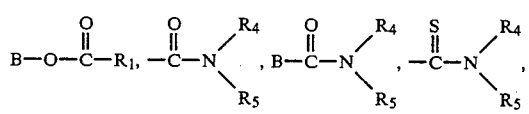

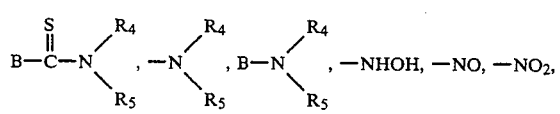

B—$NO_2$, —CN, B—CN, —NC, B—NC, —SCN, —$S(O)_n CF_3$,

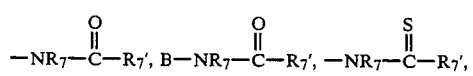

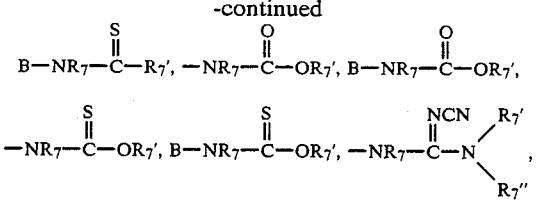

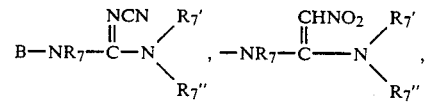

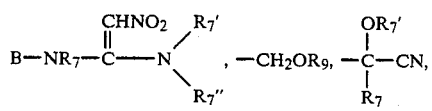

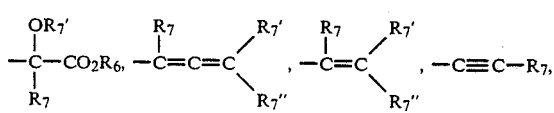

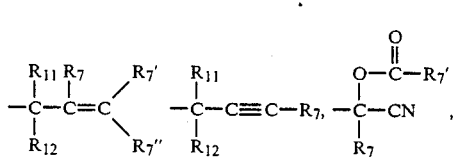

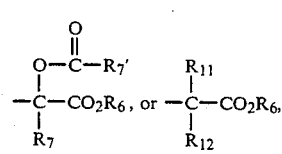

or a straight- or branched-chain alkenyl or alkynyl group having 2 to 6 carbon atoms, aryl-substituted derivatives thereof, or taken together are a cyclic alkyl of 3 to 6 bridging carbon atoms;

X represents hydrogen, lower alkyl, halogen, hydroxy, lower alkoxy, trifluoromethyl, —$NO_2$, —CN,

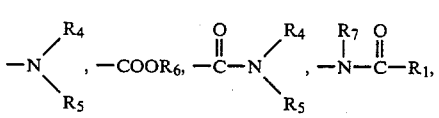

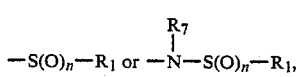

wherein n is zero, one or two with the proviso that when $R_1$ represents

n represents two;

Z represents —O—, —S—, —SO—, —$SO_2$—, —$NR_6$—, or a bond connecting T to the 5-, 6- or 8-position of the imidazo[1,2-a]pyrazine nucleus;

B represents a straight- or branched-chain lower alkylene moiety;

T represents a straight- or branched chain lower alkylene moiety and; (a) when Z is a bond connecting T and the imidazo[1,2-a]pyrazine nucleus, T represents the —OR$_7$ derivatives of said imidazo[1,2-a]pyrazine or the α(β)- or the β(γ) unsaturated derivatives of said imidazo[1,2-a]pyrazine; or (b) when Z is —O—, T also represents the allylene (—CH$_2$—CH=CH—) derivatives of said imidazo[1,2-a]pyrazine;

When T is indicated to be such unsaturated derivative or allylene, it is intended to mean the cis-isomer, the trans-isomer, or mixtures thereof although for convenience the formulas are depicted herein as mixtures. Generaly, either the cis- or trans- is the more active isomer.

m is zero to ten with the proviso that when W is Ar, m is not zero and the number of bridging carbons between Z and W is no greater than 5;

W represents hydrogen when T is allylene; or Ar, wherein Ar represents phenyl, pyridyl, thienyl, imidazolyl, furanyl or X'—, Y'—, Z'—substituted phenyl wherein each of X'—, Y'— and Z'— independently is as hereinabove defined for X; and when m is 1 to 3, W represents alkenyl, alkynyl, Z$^1$R$_6$ or Z$^1$COR$_6$, wherein Z$^1$ is —O—, —S—, —SO—, —SO$_2$— or —NR$_6$—;

Y represents —O—, —S—, —SO—, —SO$_2$— or NR$_6$—;

wherein in the above definitions;

R$_1$ represents Ar, lower alkyl,

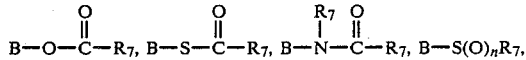

or Ar-loweralkyl;

R$_4$ and R$_5$ each independently represents hydrogen, lower alkyl, Ar, Ar-lower alkyl, lower alkoxy lower alkyl, trifluoromethyl lower alkyl, or when taken together with the nitrogen atoms to which they are attached represents a 4- to 7-membered cyclic amino or a morpholino group;

R$_6$ represents hydrogen, C$_1$— to C$_{12}$— alkyl, aryl or an arylalkyl group having up to 12 carbon atoms;

R$_7$, R$_7'$ and R$_7''$ each independently represents hydrogen or lower alkyl;

R$_8$ represents hydrogen, lower alkyl, lower alkoxy lower alkyl, trifluoromethyl lower alkyl, Ar-lower alkyl, or Ar;

R$_9$ represents

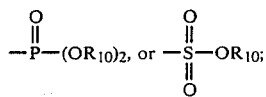

R$_{10}$ represents hydrogen, alkali metal or lower alkyl;

R$_{11}$ and R$_{12}$ each independently represents hydrogen or lower alkyl or together represent oxygen;

R$_{13}$ and R$_{14}$ each independently represents hydrogen, alkyl, aryl, or together represent —O— or —S—;

R$_{15}$ and R$_{16}$ each independently represents hydrogen, alkyl, aryl, or together represent —O— or —S—, provided that when R$_{13}$ and R$_{14}$ together represent —O— or —S—, R$_{15}$ and R$_{16}$ do not represent —O— or —S—;

p and q are each independently 0, 1 or 2 provided that when one of p and q is zero, the other is not zero.

As employed throughout this specification, the term "halogen" refers to fluoro, chloro, bromo and iodo, with chloro and fluoro being preferred. The term "lower", as it modifies such radicals as alkyl, alkylene (as used herein, "alkylene" refers to saturated divalent alkyl-derived radicals), alkene, alkoxy and the like, unless otherwise stated, means straight- and branched-chain radicals having up to six carbon atoms, e.g. methyl, ethyl, propyl, butyl, t-butyl, isopropyl, neopentyl, dimethylbutyl, propenylene, allylene (—CH$_2$—CH=CH—), ethenylene (—CH=CH—), methylene (—CH$_2$—), ethylene (—CH$_2$CH$_2$—), propylene (—CH$_2$—CH$_2$—CH$_2$—) and the like. Methyl is the preferred lower alkyl and is especially preferred at R$_2$ and/or R$_3$ in Formulas I and II. The radical

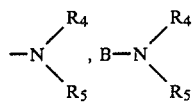

is preferably —NH$_2$, particularly at R$_3$.

"Pyridyl" includes the 2-, 3- and 4-isomers and their halogen- and lower alkyl-substituted analogs; "thienyl" includes the 2- and 3-isomers and their halogen- and lower alkyl substituted analogs; "imidazolyl" includes the 2- and 4-isomers, and their halogen- and lower alkyl-substituted analogs. When the moiety "Ar" is the X'—, Y'—, Z'—substituted phenyl radical, it is preferred that the substituents be halogen which may be in the ortho, meta and/or para positions of the phenyl group. In those compounds in which the X-substituent is other than hydrogen, it may be at one or more of the 5-, 6- or 8-positions of the imidazo[1,2-a]pyrazine nucleus which are not already substituted by the "Z—T$_m$—W" group of Formula I or by the "U" group of Formula II, said latter two groups being preferably at the 8-position. When R$_4$ and R$_5$ are other than hydrogen, it is preferred that they be methyl or ethyl. "T" preferably represents methylene (—CH$_2$—) or allylene (—CH$_2$—CH=CH—) when "Z" represents —O—, or methylene when Z represents —NH—, and ethylene (—CH$_2$CH$_2$—), ethenylene (—CH=CH—) or 1-propenylene (—CH=CHCH$_2$—) when "Z" represents a single bond.

"Pharmaceutically acceptable salts" includes salts wherein the acidic hydrogen in the carboxylic acid derivatives of this invention (e.g. wherein R$_2$=COOH) is replaced with a cation (e.g. sodium) as well as salts wherein an acidic hydrogen forms an acid addition salt with an amine, e.g. the phosphate salt of 3-amino-2-methyl-8-phenylmethoxyimidazo[1,2-a]pyrazine.

Among the pharmaceutically acceptable cationic salts contemplated for this invention are salts of alkali and alkaline earth metals, e.g. sodium, potassium, and calcium, also aluminum, as well as salts with an amine, such as an N-methylglucamine salt.

Suitable acids for the pharmaceutically acceptable acid addition salts include hydrochloric, sulfuric, phosphoric, nitric, acetic, propionic, maleic, ascorbic, citric and the like.

Both the cationic salts and acid addition salts are prepared via procedures well known in the art.

A preferred subgroup of compounds of Formula I are those wherein

R$_2$ and R$_3$ each independently represents hydrogen, lower alkyl with 1 to 3 carbon atoms, —CH$_2$OH, —CH$_2$CN, —NH$_2$, —NO,

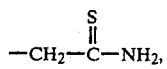

—CH$_2$—O—CO—R$_1$ (wherein R$_1$ represents methyl, ethyl, propyl, isopropyl, t-butyl or dimethylaminomethyl) or —S(O)$_n$—CH$_3$ (wherein n is zero, one or two);

X represents hydrogen;

Z represents —O—, —NH—, —S— or a single bond;

T represents a branched- or straight-chain lower alkylene group; and when Z is a single bond, T also represents an ethenylene group or a propenylene group and when Z is —O—, T represents an allylene group; and W represents hydrogen when T is allylene and Z is —O—; or Ar, wherein Ar is selected from substituted-phenyl, phenyl, thienyl or pyridyl groups, wherein there are one or more substituents on the phenyl group independently selected from —H, —Cl, —F, —CH$_3$, —t-butyl, —CF$_3$, —OCH$_3$, —CN and —OH.

A more preferred subgroup of compounds of the preferred subgroup of Formula I are those substituted at the 8-position by "Z—T$_m$—W" and W is phenyl or 3-thienyl.

Preferred compounds of Formula I are represented by the following formula:

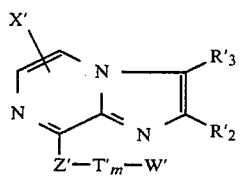

wherein

R'$_2$ and R'$_3$ independently represent —H, —CH$_3$, —CH$_2$OH, —CH$_2$CN, —NO or —NH$_2$;

X' represents hydrogen;

Z' represents —O—, —NH— or a single bond;

T'$_m$ represents —CH$_2$—, —CH$_2$—CH$_2$—,

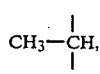

—CH$_2$CH$_2$CH$_2$—, —CH=CH— or —CH=CH—CH$_2$—; and

W' represents Ar wherein Ar is phenyl, o- or p-fluorophenyl, p-chlorophenyl, 2,4,6-trimethylphenyl, 2-thienyl or 3-thienyl.

The most preferred compounds of Formula I are those substituted by "Z—T$_m$—W" at the 8-position wherein:

R$_2$ and R$_3$ independently represent —H, —CH$_3$, —CH$_2$CN, —NH$_2$ or —CH$_2$OH;

X represents hydrogen;

Z represents —O—, —NH—, or a single bond;

when Z represents —O— or —NH—, T$_m$ represents —CH$_2$—, and when Z represents a single bond, T$_m$ represents —CH$_2$CH$_2$—, —CH=CH— or —CH=CH—CH$_2$—; and W represents Ar wherein Ar is phenyl or 3-thienyl.

Other preferred compounds having the substituents as defined in Formula I' can be substituted at the 5-, 6- or 8-positions by "Z'—T'$_m$—W'" although those substituted at the 8-position are more preferred.

Thus, the preferred "Z—T$_m$—W" substituents of Formula I include phenylmethoxy, phenylmethanamino, thienylmethoxy, thienylmethanamino, phenylethyl, thienylethyl, 2-phenylethenyl or 3-phenyl-1-propenyl.

Preferred compounds of Formula II include those wherein

R$_2$ and R$_3$ each independently represent hydrogen, methyl, —CH$_2$OH, —CH$_2$CN, —CH$_2$OCOCH$_3$,

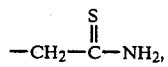

—NH$_2$ or —NO;

X represents hydrogen;

U represents —CH$_2$—O—Ar, wherein Ar is phenyl, o- or p-fluorophenyl, p-chlorophenyl, 2,4,6-trimethylphenyl, 2-thienyl or 3-thienyl. More preferred compounds are wherein the "U" group is phenoxymethyl and the most preferred compounds are those in which "U" is at the 8-position of the imidazo[1,2-a]pyrazine nucleus.

Examples of imidazo[1,2-a]pyrazine compounds within the scope of this invention are:

1. 2,3-Dimethyl-8-phenylmethoxyimidazo[1,2-a]pyrazine;
2. 3-Amino-2-methyl-8-phenylmethoxyimidazo[1,2-a]pyrazine;
3. 2-Methyl-8-phenylmethoxyimidazo[1,2-a]pyrazine-3-acetonitrile;
4. 8-(4-Fluorophenylmethoxy)-2-methylimidazo[1,2-a]pyrazine-3-thioacetamide;
5. 3-Amino-8-[2-(4'-chlorophenyl)ethyl]-2-methylimidazo[1,2-a]pyrazine;
6. 2-Methyl-3-nitroso-8-(2-phenylethyl)imidazo[1,2-a]pyrazine;
7. 3-Amino-2-methyl-8-(3-phenyl-1-propenyl)imidazo[1,2-a]pyrazine;
8. 2-Methyl-8-(3-phenyl-1-propenyl)imidazo[1,2-a]pyrazine-3-acetonitrile;
9. 3-Amino-2-methyl-8-(2-phenylethenyl)imidazo[1,2-a]pyrazine;
10. 8-(2-Fluorophenylmethoxy)-3-hydroxymethyl-2-methylimidazo[1,2-a]pyrazine;
11. 3-Amino-2-methyl-8-[2-(3-thienyl)ethyl]imidazo[1,2-a]pyrazine;
12. 3-Acetoxymethyl-2-methyl-8-(4-fluorophenylmethoxy)imidazo[1,2-a]pyrazine;
13. 8-Phenylmethanamino-2-methylimidazo[1,2-a]pyrazine-3-acetonitrile;
14. 2-Amino-3-methyl-8-phenylmethoxyimidazo[1,2-a]pyrazine;
15. 2,3-Dimethyl-8(3-phenyl-1-propenyl)imidazo[1,2-a]pyrazine;
16. 2-Hydroxymethyl-3-methyl-8-(2-phenylethyl)imidazo[1,2-a]pyrazine;
17. 2,3-Diamino-8-phenylmethoxyimidazo[1,2-a]pyrazine;

18. 2-Methyl-3-ethylamino-8-phenylmethoxyimidazo[1,2-a]pyrazine;
19. 2-Methyl-8-(2-phenylethenyl)imidazo[1,2-a]pyrazine-3-acetonitrile;
20. 2,3-Dimethyl-8-(2-phenylethenyl)imidazo[1,2-a]pyrazine;
21. 2-Methyl-3-amino-8-[2-(3-thienyl)ethenyl]imidazo[1,2-a]pyrazine;
22. 2-Methyl-8-[2-(3-thienyl)ethenyl]imidazo[1,2-a]pyrazine-3-acetonitrile; and
23. 2,3-Dimethyl-8-[2-(3-thienyl)ethenyl]imidazo[1,2-a]pyrazine.

DETAILED DESCRIPTION OF THE INVENTION

There is no single generic preparative method by which the compounds of this invention can be prepared because of the nature and positioning of the various substituents on the imidazo[1,2-a]pyrazine nucleus. Generally, the compounds can be prepared by known methods using as starting materials either known compounds or compounds which can be made by conventional means. The particular methods and sequence of reactions is dictated by the specific substituents and their positions. More than one sequence of reactions may be used for certain of the specific compounds or subgenera within the scope of this invention. Generally, the imidazo[1,2-a]pyrazine compounds of this invention can be prepared by reacting the appropriate 3-, 5- and/or 6-substituted, preferably the 3-substituted-2-aminopyrazine with a reactive halogenated carbonyl compound, i.e. a halogenated aldehyde or ketone as shown in the following reaction Scheme I.

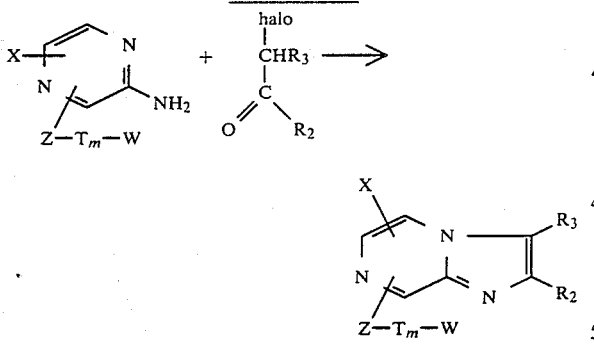

The reactants are heated together either neat or in a nonreactive anhydrous solvent under basic or neutral conditions at temperatures of from about 50° C. to 150° C.

For example, condensation of a 2-amino-3-chloropyrazine with chloroacetone gives an 8-chloro-2-methylimidazo[1,2-a]pyrazine as shown the following reaction Scheme II.

SCHEME II

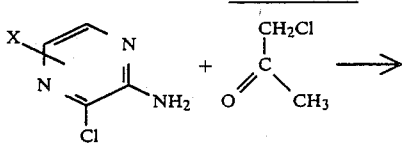

-continued
SCHEME II

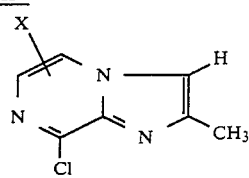

An imidazo[1,2-a]pyrazine with a 2-methyl and a 3-carboethoxy substituent can be prepared by reacting a 2-amino-3-chloropyrazine with ethyl 2-chloroacetoacetate as shown in the following reaction Scheme III.

SCHEME III

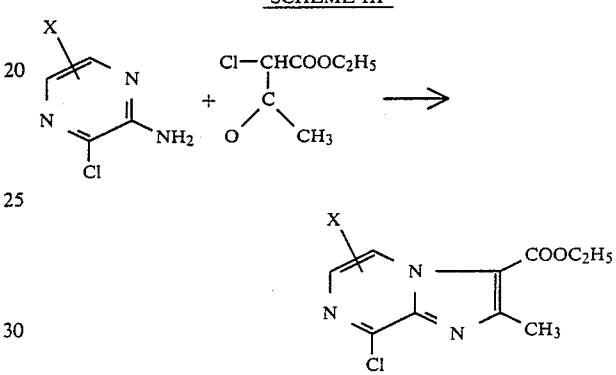

Similarly, condensation of the 2-aminopyrazine with 3-bromo-2-butanone gives the 2,3-dimethylimidazo[1,2-a]pyrazine as shown in the following reaction Scheme IV.

SCHEME IV

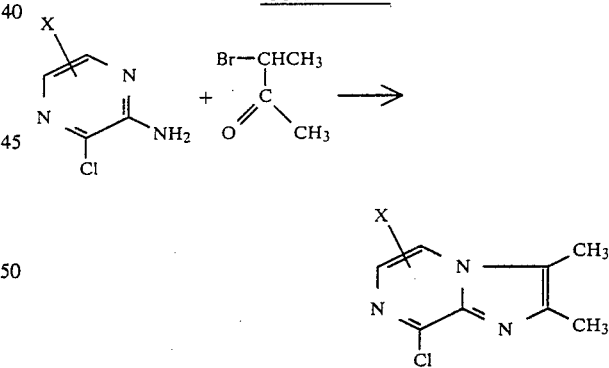

Each of the products resulting from reaction Schemes I, II, III and IV can be converted to a compound with a desired substituent on the pyrazine ring in place of the chlorine depicted. This is accomplished by reacting, e.g. 8-chloroimidazo[1,2-a]pyrazine with an appropriate nucleophile to give the corresponding 8-substituted imidazo[1,2-a]pyrazine.

For example, treating 8-chloro-2,3-dimethylimidazo[1,2-a]pyrazine with sodium phenylmethoxide yields an 8-phenylmethoxy-2,3-dimethylimidazo[1,2-a]pyrazine as shown in rection Scheme V.

SCHEME V

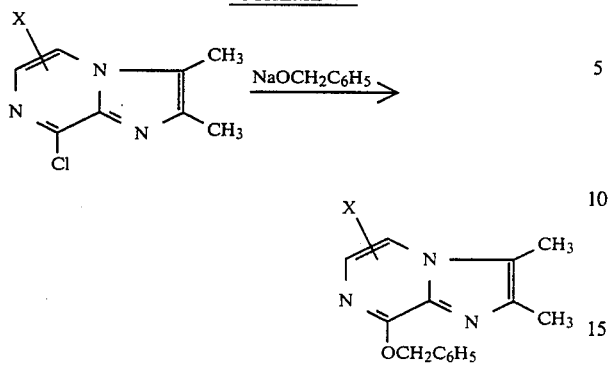

2-Aminopyrazines containing substituents in the 5- and 6-positions can be used in similar analogous reactions to prepare imidazo[1,2-a]pyrazines substituted in the 6- and 5-positions, respectively.

Various 3-substituted derivatives of the imidazo[1,2-a]pyrazine compounds of this invention can be prepared from the 3-hydrogen or 3-carboethoxy derivative by conventional procedures. For example, the 3-hydrogen compound can be converted to the 3-nitro derivative using a mixture of sulfuric and nitric acids. The 3-nitro derivative can then be reduced to the corresponding 3-amino compound. Alternatively, the 3-hydrogen compound can be nitrosated to the corresponding 3-nitroso compound using a solution of nitrous acid or an alkyl nitrite, e.g. n-butyl nitrite. The 3-amino derivative can be produced by reduction of the 3-nitroso derivative, e.g. with zinc and acetic acid. The preceding reactions are illustrated in the following reaction Scheme VI.

SCHEME VI

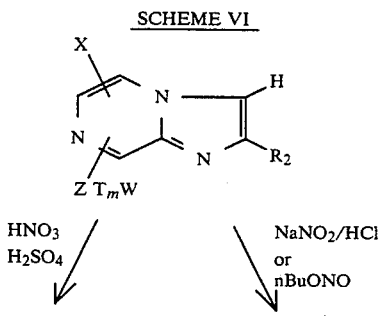

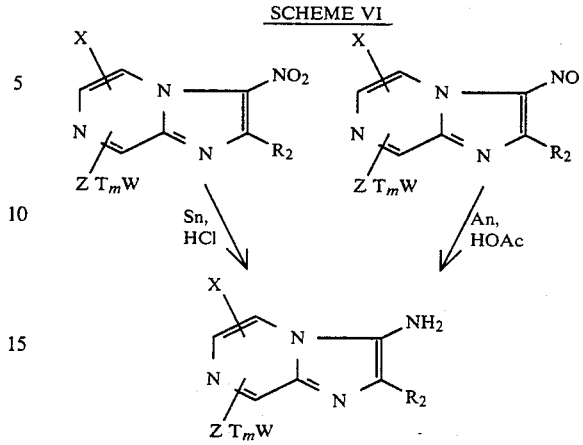

The 3-carboalkoxy compounds can be converted to the corresponding 3-hydroxymethyl derivative by reaction with lithium aluminum hydride in tetrahydrofuran (THF) as shown in the following reaction Scheme VII.

SCHEME VII

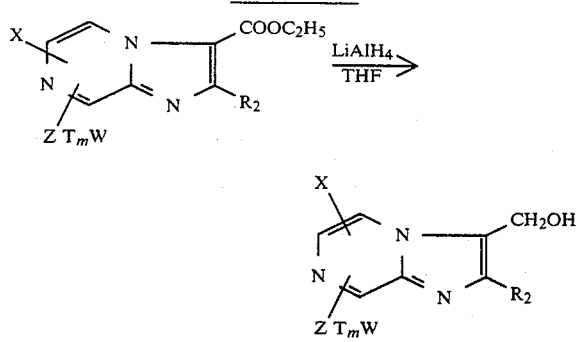

The 3-hydroxymethyl derivative can then be converted to an ester by reaction with an acid halide or an acid anhydride in an inert solvent.

In addition, the 3-hydroxymethyl derivative, upon reaction with phosphorous oxychloride is converted to the 3-chloromethyl derivative. This latter derivative, upon reaction with an alkali metal cyanide, e.g. sodium cyanide, in a suitable solvent such as dimethylsulfoxide (DMSO), ethanol or dimethylformamide (DMF) gives the corresponding 3-cyanomethyl derivative. The corresponding 3-thioacetamide derivative can be produced by reacting the 3-cyanomethyl compound with hydrogen sulfide in pyridine. The above reactions are illustrated in the following reaction Scheme VIII.

SCHEME VIII

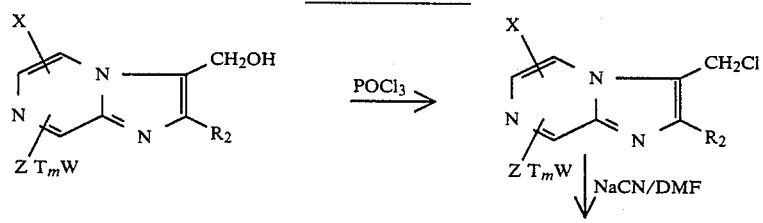

SCHEME VIII

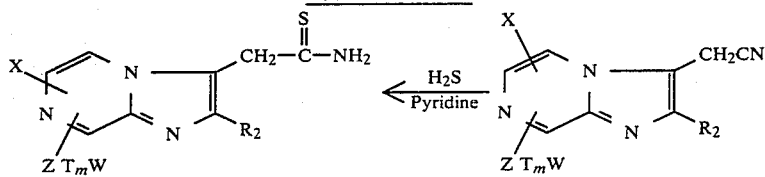

The above reactions, while described to show how nitro, amino, nitroso, alkyl, hydrogen, ester, hydroxymethyl, chloromethyl, cyanomethyl (acetonitrile) and thioacetamide substituents can be introduced to the three position of the imidazo[1,2-a]pyrazine, and how alkyl can be introduced to the two position, are equally applicable for the introduction of other substituents at those positions by using reactants which are analogously substituted.

For example, an amino group can be introduced at the two position of a 3-substituted-imidazo[1,2-a]pyrazine by reacting it with a mixture of nitric acid and sulfuric acid to introduce a nitro-substituent at the two position, then reducing the nitro group to an amino group using conventional reaction conditions.

Use of a 2-amino-3-arylalkylpyrazine to produce an imidazo[1,2-a]pyrazine results in a compound wherein "Z" of Formula I is a bond connecting "$T_m$—W" of Formula I at the 8-position thereof. Other transformations to the compounds of this invention wherein "Z" represents sulfur-, sulfinyl- and sulfonyl-moieties are also effected via standard methods for introducing these moieties to a pyrazine ring, e.g. after sulfur is introduced, it can be oxidized to sulfinyl or sulfonyl. Similarly, the preparations of the tetrahydro and perhydro derivatives are effected in accordance with reduction methods which are well known for introducing hydrogen to heterocyclic and aromatic rings.

In compounds of Formula II, the substituent U wherein Y is —O—, —S— or —NR$_6$— may be introduced by chemical modification of the corresponding imidazo[1,2-a]pyrazine having a formyl group at one of positions 5-, 6- or 8-. Thus, for example, 8-formylimidazo[1,2-a]pyrazine having R$_2$ and R$_3$ substituents as defined hereinabove, upon reduction with sodium borohydride, is converted to the corresponding 8-hydroxymethyl derivative which can be used as an intermediate for preparing compounds of Formula II wherein Y is —O— or —S—. Etherification of the 8-hydroxymethyl intermediate, e.g. by treatment with sodium hydride followed by reaction of the resulting sodium salt with an arylalkyl halide, produces an 8-arylalkoxymethyl derivative of Formula II. Alternatively, replacement of the hydroxyl group with a leaving group, e.g. tosyl, followed by displacement thereof with an aryloxide alkali metal salt, e.g. sodium phenoxide, produces an 8-aryloxymethyl derivative of Formula II.

Similarly, replacement of the hydroxyl group with a good leaving group followed by displacement thereof with an appropriate thio reagent, e.g. an alkali metal salt of an arylalkylthiol or an arylthiol, produces compounds of Formula II wherein Y is sulfur, e.g. an 8-arylalkylthiomethyl- or an 8-arylthiomethyl-derivative, respectively.

An imidazo[1,2-a]pyrazine having a formyl group at one of positions 5-, 6-, or 8- is also a useful intermediate in introducing substituents of Formula II wherin Y is nitrogen. Thus, for example, reaction of 8-formylimidazo[1,2-a]pyrazine having R$_2$ and R$_3$ substituents as defined hereinabove with an arylamine or an arylalkylamine, followed by reduction of the resulting imines, produces 8-arylaminomethyl- and 8-arylalkylaminomethyl derivatives of Formula II. Treatment of the foregoing secondary amine derivatives with a base followed by reaction with a hydrocarbon halide yields the corresponding tertiary amine derivatives of formula II, i.e. compounds wherein Y is NR$_6$ with R$_6$ being other than hydrogen.

Compounds of this invention having an olefinic functionality at positions 5-, 6- or 8-, i.e. compounds of Formula I wherein Z is a bond and T is $\alpha(\beta)$- or $\beta(\gamma)$-unsaturated lower alkylene, are derived from the corresponding formylimidazo[1,2-a]pyrazines having R$_2$ and R$_3$ substituents as defined hereinabove above, upon reaction thereof under Wittig conditions or modifications thereof.

Compounds of Formula I wherein Z represents —SO— or —SO$_2$— may be obtained by oxidizing the corresponding compound wherein Z represents —S—, according to procedures well known in the art.

Numerous standard reactions may be applied for transferring one type of substituent R$_2$ an/or R$_3$ into another type. Thus, for example, for preparing compounds of Formula I wherein R$_3$ represents the group BCN, the following processes may be applied.

1. Subject a compound of Formula I wherein R$_2$, X, T, Z and Ar are as defined for Formula I and R$_3$ represents either BCONH$_2$ or

to dehydration by treating a starting compound with a suitable dehydrating agent in an inert solvent. Preferred dehydrating agents are (CF$_3$CO)$_2$O (in pyridine), SeO$_2$, POCl$_3$, and the like. The starting compounds may be obtained according to standard procedures.

2. Treat a compound of Formula I wherein R$_2$, X, T, Z and Ar are as defined for Formula I and R$_3$ represents the group

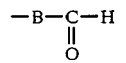

with suitable reagent, e.g. Tosyl—CH$_2$—NC in the presence of potassium-t-butoxide whereby the formyl function is replaced by CH$_2$CN.

3. Treat a compound of Formula I wherein R$_2$, X, T, Z and Ar are as defined for Formula I and R$_3$ represents the group —B—COOR with a suitable reagent, e.g. dimethylaluminumamide resulting in a compound where R$_3$ is —BCN.

4. Treat a compound of Formula I wherein $R_2$, X, T, Z and Ar are as defined for Formula I and $R_3$ represents the group

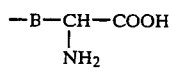

with NaOCl under standard conditions.

5. Subject a compound of Formula I wherein $R_2$, X, T, Z and Ar are as defined for Formula I and $R_3$ represents a group $B-CH_2NO_2$ to a reductive dehydration, e.g. with $PCl_3$ and the like in pyridine to give the desired nitrile.

6. React a compound of Formula I wherein $R_2$, X, T, Z and Ar are as defined for Formula I and $R_3$ represents H with a compound of the formula Hal—B—CN wherein Hal is chlorine or bromine, in the presence of a Lewis acid, e.g. aluminum chloride, zinc chloride, boron chloride and the like, or a phase transfer catalyst.

7. Subject a compound of Formula I wherein $R_2$, X, T, Z and Ar are as defined for Formula I and $R_3$ represents the group

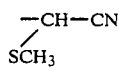

to a reduction, preferably with Raney-nickel whereby the —$SCH_3$ group is replaced by a hydrogen atom. The starting compound may be obtained by reacting a compound of Formula I wherein $R_3$ represents hydrogen with $CH_3-S-CH(Cl)CN$ by means of a Friedel Crafts catalyst, e.g. $SnCl_4$, $TiCl_4$, $AlCl_3$, and the like.

In addition to modifying various $R_3$ groups into —B—CN groups as described in the above reactions, other transformations may be carried out, e.g. as indicated in the following tables:

TABLE I

| STARTING $R_3$ | CHEMICAL REACTION | RESULTING $R_3$ |
|---|---|---|
| —$COOC_2H_5$ | reduction ($LiAlH_4$) | —$CH_2OH$ |
| —$CH_2CN$ | reaction with alkylhalide, base | alkyl<br>\|<br>—CH—CN |
| —CN | reduction with $LiAlH_4$ | —$CH_2NH_2$ |
| —$CH_2NH_2$ | 1. reaction with methyliodide<br>2. followed by reaction with metal cyanide | —$CH_2CN$ |
| —CN | saponification | —COOH |
| —BOH | reaction with NaH and $ClCON(CH_3)_2$ | —B—$OCON(CH_3)_2$ |
| —BCN | hydrolysis | —$BCONH_2$ |
| —BCN | treatment with $H_2S$ | —$BCSNH_2$ |
| —BOH | treatment with $SOCl_2$ | —BCl |
| —BX″ (X″ = leaving group, e.g. halogen) | treatment with $NO_2$ | —$BNO_2$ |
| —BX″ (X″ = leaving group, e.g. halogen) | reaction with $CH_3NO_2$, base | —$BCH_2NO_2$ |
| —CHO | 1. reaction with base, $CH_3NO_2$ resulting in CH=$CHNO_2$<br>2. treatment with $NaBH_4$ | —$CH_2CH_2NO_2$ |
| H | nitration | —$NO_2$ |
| H | nitrosation | —NO |

TABLE I-continued

| STARTING $R_3$ | CHEMICAL REACTION | RESULTING $R_3$ |
|---|---|---|
| $-\overset{O}{\underset{\|}{N}}-(O)_n$ (n = 0,1) | reduction | —$NH_2$ |
| —$NH_2$ | 1. diazotization<br>2. followed by reaction with an alkali metal thiocyanate | —SCN |
| H | halogenation | —Cl<br>—Br |
| H | acylation via acid chloride or acid anhydride | —COCH=$CH_2$<br>—COC≡CH<br>—COCOOR<br>(R = H, alkyl) |
| —COCOOR (R = H, alkyl) | reduction ($NaBH_4$) | —CHOHCOOR |
| —COR (R = H, alkyl) | treatment with hydrogen cyanide | OH\\<br>$-\underset{R}{\overset{\|}{C}}-CN$ |
| OH<br>\|<br>—C—CN<br>\|<br>R<br>(R = H, alkyl) | esterification | $OCOR^1$<br>\|<br>—C—CN<br>/<br>R<br>$R^1$ = hydrocarbon |
| OH<br>\|<br>—C—CN<br>\|<br>R<br>(R = H, alkyl) | etherification | $OR^1$<br>\|<br>C—CN<br>\|<br>R<br>($R^1$ = hydrocarbon) |
| —$CH_2OH$ | 1. (a) Phosphorylation (b) or sulfonylation<br>2. followed by esterification or treatment with an alkali metal base | (a) $-CH_2-O\overset{O}{\underset{\|}{P}}\overset{-OR}{\underset{OR}{\diagdown}}$<br>R = H, alkali metal or alkyl<br>(b) $-CH_2-O\overset{O}{\underset{\|}{S}}\overset{-OR}{\underset{O}{\diagdown}}$ |
| —$CH_2OH$ | alkylation with NaH and $ClCH_2SCH_3$ | —$CH_2OCH_2SCH_3$ |
| —$CH_2OH$ | alkylation with NaH and $ClCH_2SC_6H_5/NaI$ | —$CH_2OCH_2SC_6H_5$ |
| —$CH_2OH$ | alkylation with NaH and $R-\overset{O}{\underset{\|}{C}}-XCH_2Cl/NaI$ (X = O, S, NR; R = H, $CH_3$) | —$CH_2OCH_2XCOR$ |

Equally the various possibilities of $R_2$ may, where appropriate, be transformed into other $R_2$-substituents by reactions such as those outlined for $R_3$ in the processes described above. Also, the following are other transformations which may be carried out at the two-position to modify the $R_2$-function; which transformations may also be carried out, where appropriate, to modify the $R_3$-function at the three-position.

TABLE II

| STARTING $R_2$ | CHEMICAL REACTION | RESULTING $R_2$ |
|---|---|---|
| $\begin{array}{c}CH_3\\|\\-CH-COOC_2H_5\end{array}$ | alkylation with NaH and $CH_3I$ | $-C-(CH_3)_2$ / $COOC_2H_5$ |
| $-(CH_2)_nCOOR$ $R = H$, alkyl $n = 0,1$ | Reduction | $-(CH_2)_nCHO$ |
| $-(CH_2)_nCOOH$ | organometallic reagent (e.g. alkyl Lithium) | $-(CH_2)_n-\overset{O}{\overset{\|}{C}}-R$ ($R$ = alkyl) |
| $-(CH_2)_nCHO$ ($n = 0,1$) | Wittig process | $-(CH_2)_nCH=CH_2$ |
| $-(CH_2)_n-COR$ ($n = 0,1$; $R$ = alkyl) | Wittig process | $-(CH_2)_nCR=CH_2$ |
| $-(CH_2)_nCH=CH_2$ ($n = 0,1$) | halogen addition and elimination | $-(CH_2)_nC\equiv CH$ |
| $\begin{array}{c}R\\|\\-CHOH\end{array}$ ($R$ = H, alkyl) | 1. replacement of OH with leaving group (e.g. tosyl) 2. nucleophilic displacement with $LiC\equiv CH$ | $-CHRC\equiv CH$ |
| $-CHR-C\equiv CH$ ($R$ = H, alkyl) | isomerization (acid or base) | $\begin{array}{c}R\\|\\-C=C=CH_2\end{array}$ |
| $-OH$ | reaction with $P_2S_5$ | $-SH$ |
| $-OH$ | etherification | $-OR$ |
| $-SH$ | etherification | $-SR$ ($R$ = alkyl) |
| $-NHCOOR$ ($R$ = H, alkyl) | hydrolysis | $-NH_2$ |

The imidazo[1,2-a]pyrazine compounds of this invention are useful in the treatment of peptic ulcers. They display chemotherapeutic activity which enables them to relieve the symptoms of peptic ulcer disease, including stress ulceration, and promote healing of gastric and/or duodenal ulcers. The antiulcer activity of the compounds of this invention is identified by tests which measure their cytoprotective effect (also referred to as mucoprotective effect) and antisecretory effects in rats. The compounds are also useful as conjuctive therapeutic agents for coadministration with such anti-inflammatory/analgesic agents as aspirin, indomethacin, phenylbutazone, ibuprofen, naproxen, tolmetin and other agents having the untoward side effect of contributing irritation and damage to the gastrointestinal tract.

The compounds of this invention are evaluated for their activity characteristics by standard biological testing procedures.

In the testing procedures they are evaluated on an absolute basis and on a comparative basis with compounds known to possess the activity useful for the treatment and/or prevention of peptic ulcer disease and drug induced gastric ulceration. Such tests include testing for antisecretory effects in rats with pyloric ligation techniques. The test compounds are administered either intraperitoneally or orally in appropriate and well-defined and well-known vehicles.

In cytoprotective tests in rats in which ethanol is employed to induce gastrointestinal damage, the compounds of this invention are found to be effective for the oral treatment of the ulcerative disease states mentioned herein.

The compounds are effective when administered orally at doses of about 0.5 to 50 mg/kg of body weight per day. Preferably the total dosages are administered in 2-4 divided doses per day.

When administered parenterally, e.g. intravenously, the compounds are administered at a dosage range of about 0.01 to 10 mg/kg body weight in single or multiple daily doses. Of course, the dose will be regulated according to the judgment of the attending clinician depending on factors such as the degree and severity of the disease state and age and general condition of the patient being treated. The usual dosage range for the preferred compounds of this invention is an oral dose of about 75 to 1600 mg/day, preferably 600 to 800 mg/day, in two to four divided doses. This dosage regimen achieves relief of the symptoms of peptic ulcer disease and promotes the healing of gastric and/or duodenal ulcers.

To treat peptic ulcer disease, gastric and duodenal ulcers, and prevent and treat drug-induced gastric ulceration, the active compounds of this invention can be administered in unit dosage forms such as tablets, capsules, pills, powders, granules, sterile parenteral solutions or suspensions, suppositories, mechanical delivery devices, e.g. transdermal, and the like. Such dosage forms are prepared according to standard techniques well known in the art.

The following examples illustrate the preparation of compounds and compositions of this invention. All temperatures are in degrees Celsius.

EXAMPLE 1

A stirred mixture of 6.38 g of 2-amino-3-chloropyrazine, 7.44 g of 3-bromo-2-butanone and 2.5 ml of anhydrous methanol in a bath maintained at 100° was treated for 18 hours. The mixture was cooled to room temperature and partitioned between aqueous sodium bicarbonate and methylene chloride. The layers were separated and the aqueous phase extracted with methylene chloride. The organic extracts were combined and dried over anhydrous sodium sulfate. The solvent was removed at reduced pressure and the residue was chromotographed on silica gel. A mixture of 8-chloro- and 8-bromo-2,3-dimethylimidazo[1,2-a]pyrazine, m.p. 169.5°-172°, was isolated upon crystallization of the residue from ethyl acetate.

EXAMPLE 2

A solution of 3.13 g benzyl alcohol in 10 ml of dry dimethylformamide (DMF) was added to a stirred suspension of 1.39 g of 50% sodium hydride-mineral oil in 20 ml dry DMF and stirred at room temperature for two hours. A cooled (about 15°) solution of 4.79 g of the product of Example 1 in 50 ml dry DMF was added and the reaction mixture was stirred at room temperature for 16 hours. The reaction mixture was concentrated on a rotary evaporator under reduced pressure (55°/0.2 torr.), and the residue was partitioned between water and methylene chloride.

The organic and aqueous layers were separated and the aqueous phase was extracted with methylene chloride. The combined extracts were washed with water and brine, dried over magnesium sulfate and the solvent removed under reduced pressure. The residue was triturated with cold isopropyl ether. The solid was isolated by filtration and recrystallized from methanol:isopropyl ether to obtain 2,3-dimethyl-8-phenylmethoxyimidazo[1,2-a]pyrazine, as determined by spectroscopic and combustion analysis, m.p. 104.5°-109.5°.

EXAMPLE 3

A mixture of 0.53 g of 2-amino-3-chloropyrazine and 0.84 g of 90% chloroacetone was heated at 100° for three hours.

Then 0.41 g of triethylamine was added and the heating was continued for another 17 hours. Methylene chloride and aqueous sodium bicarbonate were added to the reaction mixture which was stirred vigorously. The organic and aqueous layers were separated and the aqueous phase extracted with methylene chloride. The organic extracts were combined, washed with water and dried over anhydrous magnesium sulfate. The solvent was removed under reduced pressure, and the residual tar was stirred with 1:1 hexane-ether. The insolubles were removed and the solvent evaporated under reduced pressure, yielding 8-chloro-2-methylimidazo[1,2-a]pyrazine, m.p. 127.5°–130°.

EXAMPLE 4

A solution of 1.84 g of benzyl alcohol in 10 mg dry DMF was added to a stirred suspension of 0.86 g of 50% sodium hydride-in-mineral oil in 5 ml of dry DMF and the mixtures stirred at room temperature for 30 minutes.

A cooled (ca. 10°–15°) solution of 2.60 g of 8-chloro-2-methylimidazo[1,2-a]pyrazine in 15 ml of dry DMF was added to the mixture, and the reaction mixture was stirred at room temperature for 16 hours. The reaction mixture was concentrated under reduced pressure and the residue triturated with ether and filtered to obtain 8-phenylmethoxy-2-methylimidazo[1,2-a]pyrazine, as determined by spectroscopic and combustion analysis, m.p 99.5°–101.5°.

EXAMPLE 5

A solution of 14.2 g 2-methyl-8-phenylmethoxyimidazo[1,2-a]pyrazine, 129.3 g n-butyl nitrite and 142 ml p-dioxane was heated under reflux for 0.5 hr. and decanted from a small amount of gum. The supernatant solution was stirred under vacuum (40°/0.1 mm) and the residue azeotroped with cyclohexane to give 2-methyl-3-nitroso-8-phenylmethoxyimidazo[1,2-a]pyrazine as a soft, green solid which was identified by pmr and ms and immediately reduced (as in Example 6) without further purification.

EXAMPLE 6

2-Methyl-3-nitroso-8-phenylmethoxyimidazo[1,2-a]pyrazine (18.3 g) was dissolved in 280 ml acetic acid and diluted using 140 ml water and the solution cooled to 18°; additional acetic acid (100 ml) was then added. Zinc powder (19.2 g) was added in portions over 10 minutes at 18°–30° and then stirred 2 hrs. at room temperature.

The reaction mixture was concentrated in vacuo at 45° and the residue dissolved in 700 ml of a mixture of dichloromethane/water (5/2, V/V) and basified with 100 ml 2.5M sodium hydroxide. The resultant suspension was filtered through a celite pad, the filter cake washed with dichloromethane and the combined filtrate and washings separated. The aqueous layer was extracted with dichloromethane (3×100 ml) and the extracts were combined and dried over anhydrous sodium sulfate. The solvent was removed in vacuo to leave a brown solid. Flash chromotography on silica gel using ethyl acetate gave 3-amino-2-methyl-8-phenylmethoxyimidazo[1,2-a]pyrazine, mp 126.5°–133°. Recrystallization from ethyl acetate gave an analytical sample, mp 134.5°–136°. Treatment of the free base with etheral hydrogen chloride gave 3-Amino-2-methyl-8-phenylmethoxyimidazo[1,2-a]pyrazine hydrochloride, mp 119.5°–120.5° (dec).

The following formulations exemplify some of the dosage forms in which the compounds of this invention may be employed. In each, the active ingredient is designated by the term "Drug" which is meant to indicate one of the following compounds:

8-Phenylmethoxy-2-methylimidazo[1,2-a]pyrazine-3-acetonitrile;

2,3-Dimethyl-8-phenylmethoxyimidazo[1,2-a]pyrazine; and

8-Phenylmethoxy-2-methyl-3-aminoimidazo[1,2-a]pyrazine.

It is contemplated, however, that each of these exemplar compounds may be replaced by equally effective quantities of other compounds within the scope of Formulas I and II. All temperatures are in degrees Celsius.

| No. | Formulation 1 Tablets Ingredient | mg/tab | mg/tab |
|---|---|---|---|
| 1 | Drug | 25.0 | 400.0 |
| 2 | Lactose, impalpable powder USP | 114.0 | 241.5 |
| 3 | Corn starch USP | 25.0 | 50.0 |
| 4 | Corn starch as 5% paste in distilled water | 10.0 | 35.0 |
| 5 | Corn starch USP | 25.0 | 50.0 |
| 6 | Magnesium Stearate USP | 1.0 | 3.5 |
| | | 200.0 | 780.0 |

Method of Manufacture

Mix items nos. 1, 2 and 3 in a suitable blender for 5 to 15 minutes. Pass through a fine screen (#40) if necessary. Reblend for 5 to 10 minutes and granulate with item no. 4. Pass the damp granulated mass through a coarse sieve (#6) using a suitable mill. Dry the damp granules at 40° to 50° overnight. Mill the dried granules using a no. 20 screen. Add item no. 5 and blend for 5 to 10 minutes. Add item no. 6 and blend further for 3 to 5 minutes. Compress the tablet mixture into tablets of an appropriate size and weight using a suitable tableting machine.

| No. | Formulation 2 Capsules Ingredient | mg/tab | mg/tab |
|---|---|---|---|
| 1 | Drug | 25.0 | 400.0 |
| 2 | Lactose, impalpable powder USP | 144.0 | 191.5 |
| 3 | Corn starch USP | 30.0 | 105.0 |
| 4. | Magnesium Stearate USP | 1.0 | 3.5 |
| | | 200.0 | 700.0 |

Method of Manufacture

Mix items nos. 1, 2 and 3 in a suitable blender for 5 to 10 minutes. Pass through a fine screen (#40) if necessary. Reblend for 5 to 10 minutes, add item no. 4 and mix further for 3 to 50 minutes. Using a suitable machine, encapsulate the mixture into a two-piece hard gelatin capsule of appropriate size.

| Formulation 3 Suspensions | | |
|---|---|---|
| Ingredients | Formula A (mg/ml) | Formula B (mg/ml) |
| Drug | 5.0 | 80.0 |
| Sucrose | 600.0 | 600.0 |
| Benzyl alcohol | 10.0 | 10.0 |
| Methylcellulose (15 cps) | 4.0 | 4.0 |
| Polysorbate 80 | 5.0 | 5.0 |
| Vanillin | 0.2 | 0.2 |
| Purified Water q.s. | 1.0 ml | 1.0 ml |

Method of Manufacture

1. Charge approximately 40% of the final volume of purified water in a stainless steel tank. Heat to boiling. Agitate using an appropriate stirrer. Agitation should continue throughout procedure.
2. Add sucrose until it is dissolved.
3. Slowly add methylcellulose until it is well dispersed.
4. Start cooling the mixture to room temperature.
5. Add polysorbate, benzyl alcohol and vanillin until all ingredients are well dispersed.
6. Add the Drug until a uniform dispersion is formed.
7. Dilute the suspension to final volume with purified water at 25°.

| Formulation 4 Parenteral | |
|---|---|
| | mg/ml |
| Drug | 25.0 |
| Methylparaben | 1.3 |
| Propylparaben | 0.2 |
| Sodium bisulfite | 3.2 |
| Disodium edetate | 0.2 |
| Sodium sulfate | 2.6 |
| Water for injection q.s. | 1.0 ml |

Method of Manufacture

1. Dissolve parabens in a portion (approximately 85% of the final volume) of the water for injection at 65°-70°.
2. Cool to 25°-35°. Charge and dissolve sodium bisulfite, disodium edetate and sodium sulfate.
3. Charge and dissolve the Drug.
4. Bring the solution to the final volume by adding water for injection.
5. Filter the solution through 0.22-micron membrane and fill into appropriate containers.
6. Terminally sterilize the units by autoclaving.

| Formulation 5 Injectable Suspension | |
|---|---|
| | mg/ml |
| Drug (Sterile) | 50.0 |
| Benzyl alcohol | 9.0 |
| Methylparaben | 1.8 |
| Propylparaben | 0.2 |
| Sodium carboxymethylcellulose | 5.0 |
| Polyethylene Glycol 4000 | 10.0 |
| Povidone | 5.0 |
| Sodium Citrate | 15.0 |
| Disodium edetate | 0.1 |
| Water for injection q.s. | 1.0 ml |

Method of Preparation

1. Dissolve parabens in a portion of water for injection at 65°-70°.
2. Cool to 25°-35°. Charge and dissolve benzyl alcohol, sodium citrate, disodium edetate, PEG 4000, povidone and sodium carboxymethylcellulose.
3. Filter the solution and sterilize by autoclaving.
4. Make a slurry of the sterile Drug and pass it through a colloid mill.
5. Mix it well with solution from Step 3 and pass it through the mill.
6. Bring the suspension to the final volume/weight and fill into sterile containers.

| Formulation 6 Suppositories | |
|---|---|
| A. Formula | mg/supp |
| Drug | 5.0 |
| Cocoa butter | 1995.0 |
| | 2000.0 mg (2.0 g.) |

Procedure

1. Melt cocoa butter to about 32°-35°.
2. Blend Drug into cocoa butter until well dispersed.
3. Pour into teflon-coated mold and congeal in refrigerator. Keep in refrigerator for an appropriate length of time.
4. Remove suppositories from mold.

| B. Formula | mg/supp |
|---|---|
| Drug | 100.0 |
| PEG 1000 | 1824.0 |
| PEG 4000 | 76.0 |
| | 2000.0 mg (2.0 g.) |

Procedure

1. Melt PEG 1000 and PEG 4000 in one container to 50°.
2. Add Drug to mixture. Blend until well dispersed.
3. Pour into mold and congeal in refrigerator. Keep in refrigerator for an appropriate length of time.
4. Remove suppositories from mold.

Since all the compounds within the large class of compounds encompassed by this invention are not equally therapeutically potent, certain subgroups and certain specific compounds have been found to be preferred for their therapeutic utility. Preferred are those compounds wherein the imidazol[1,2-a]pyrazine nucleus is substituted in the 8-position through an oxygen or nitrogen atom. Another preferred group is where the "Ar" substituent represents phenyl or 3-thienyl. Another preferred group contains the "Ar" moiety linked to the 8-position of the imidazo[1,2-a]pyrazine nucleus either through a methoxy, ethoxy, methylamino or ethylamino linkage, i.e., wherein T represents methylene or ethylene; or directly through an ethylene, ethenylene or propenylene linkage, i.e. where Z is a bond and T is ethylene, ethenylene or propenylene. Another preferred group is composed of compounds containing a cyanomethyl, an amino or an alkyl substituent, particularly, methyl at the 2-position and methyl or amino at the 3-position. Still another preferred group is composed of compounds having a hydroxyalkyl, preferably hydroxymethyl, at the 2-position or the 3-position. Preferred specific compounds include those imidazo[1,2-a]pyrazines of Formulas I and II having the following substituents:

| $R_2$ | $R_3$ | X | Z | T | (m) | W |
|---|---|---|---|---|---|---|
| $CH_3$ | $CH_2CN$ | H | O | $CH_2$ | 1 | phenyl |
| $CH_2OH$ | $CH_2CN$ | H | O | $CH_2$ | 1 | phenyl |
| $CH_3$ | $CH_2CN$ | H | O | $CH_2$ | 1 | thienyl |
| $CH_3$ | $NH_2$ | H | O | $CH_2$ | 1 | phenyl |
| $CH_3$ | $CH_2OH$ | H | O | $CH_2$ | 1 | phenyl |
| $CH_3$ | $CH_2CN$ | H | NH | $CH_2$ | 1 | phenyl |
| $CH_3$ | $CH_2CN$ | H | (Bond) | $CH_2$ | 2 | phenyl |
| $CH_3$ | $CH_3$ | H | O | $CH_2$ | 1 | phenyl |
| $CH_3$ | $NH_2$ | H | O | $CH_2$ | 1 | thienyl |
| $CH_3$ | $NH_2$ | H | (Bond) | $CH_2$ | 2 | phenyl |
| $CH_3$ | $NH_2$ | H | NH | $CH_2$ | 1 | phenyl |
| $CH_2CN$ | $CH_3$ | H | O | $CH_2$ | 1 | phenyl |
| $CH_2CN$ | $CH_3$ | H | NH | $CH_2$ | 1 | thienyl |
| $CH_2CN$ | $CH_3$ | H | (Bond) | $CH_2$ | 2 | thienyl |
| $CH_2CN$ | $CH_3$ | H | (Bond) | $CH_2$ | 3 | thienyl |
| $CH_2CN$ | $CH_3$ | H | (Bond) | $CH_2$ | 3 | phenyl |
| $CH_3$ | $NH_2$ | H | (Bond) | $-CH=CHCH_2-$ | 1 | phenyl |
| $CH_3$ | $NH_2$ | H | (Bond) | $-CH=CH-$ | 1 | phenyl |
| $CH_3$ | $NH_2$ | H | (Bond) | $-CH=CH-$ | 1 | thienyl |
| $CH_3$ | $CH_3$ | H | (Bond) | $-CH=CH-$ | 1 | phenyl |
| $CH_3$ | $CH_3$ | H | (Bond) | $-CH=CH-$ | 1 | thienyl |
| $CH_3$ | $CH_2CN$ | H | (Bond) | $-CH=CH-$ | 1 | phenyl |
| $CH_3$ | $CH_2CN$ | H | (Bond) | $-CH=CH-$ | 1 | thienyl |
| $CH_3$ | $CH_3$ | H | (Bond) | $-CH=CHCH_2-$ | 1 | phenyl |
| $CH_3$ | $CH_2CN$ | H | (Bond) | $-CH=CHCH_2-$ | 1 | phenyl |

We claim:

1. A compound represented by the formulas:

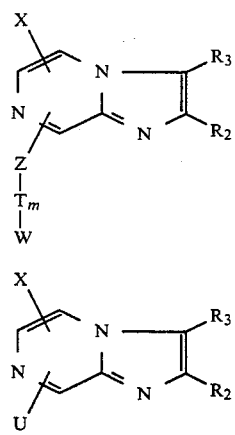

the 5,6,7,8-tetrahydro, 2,3-dihydro and perhydro derivatives thereof, and the pharmaceutically acceptable salts thereof, wherein:

U represents

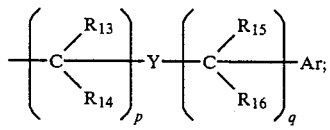

$R_2$ and $R_3$ each independently represent hydrogen, lower alkyl, trifluoromethyl, $B-CF_3$, Ar, $B-Ar$, halogen, $B-$halogen $-OR_7$, $B-OR_8$, $B-SR_6$, $-S(O)_n-R_7$, $S(O)_n-$ lower alkyl,
(wherein n is zero, one or two),

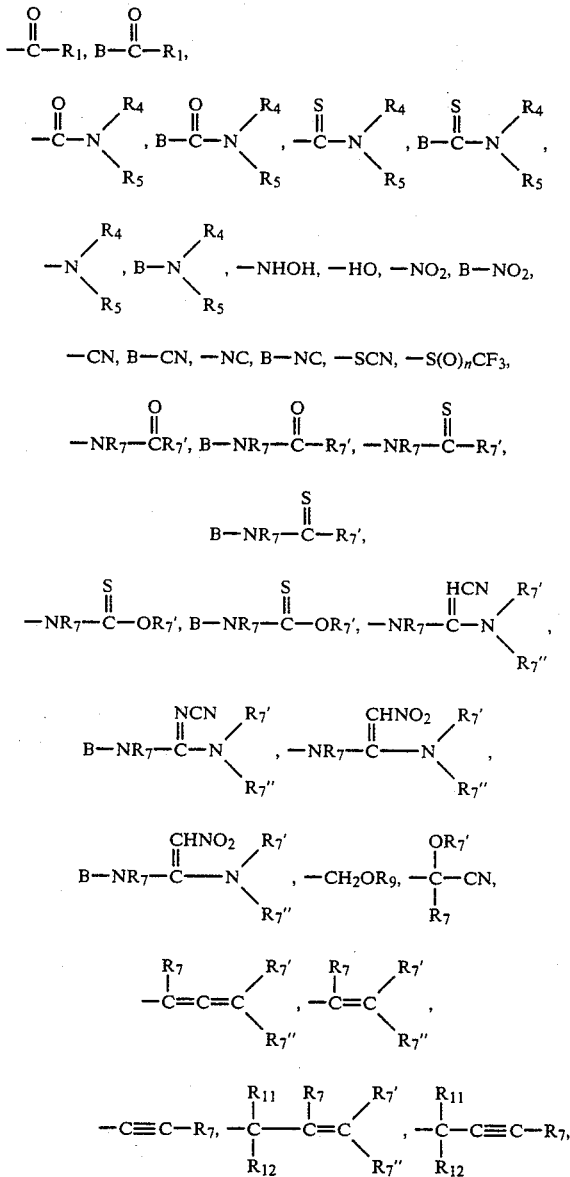

or a straight- or branched-chain alkenyl or alkynyl group having 2 to 6 carbon atoms and aryl-substituted derivatives thereof, or taken together are a cyclic alkyl of 3 to 6 bridging carbon atoms;

X represents hydrogen, lower alkyl, halogen, hydroxy, lower alkoxy, trifluoromethyl, $-NO_2$, $-CN$,

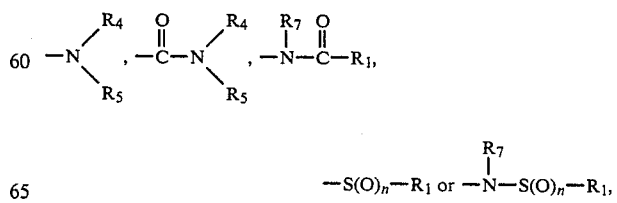

wherein n is zero, one or two with the proviso that when $R_1$ represents

n represents two;

Z represents —O—, —S—, —SO—, —SO$_2$—, —NR$_6$—, or a bond connecting T to the 5-, 6- or 8-position of the imidazo [1,2-a]pyrazine nucleus;

B represents a straight- or branched-chain lower alkylene moiety;

T represents a straight- or branched-chain lower alkylene moiety and; (a) when Z is a bond connecting T and the imidazo[1,2-a]pyrazine nucleus, T represents the —OR$_7$ derivatives of said imidazo[1,2-a]pyrazine, or the α(β)- or β(γ)-unsaturated derivatives of said imidazo[1,2-a]pyrazine, or (b) when Z is —O—, T also represents the allylene derivatives of said imidazo[1,2-a]pyrazine;

m is zero to 10 with the proviso that when W is Ar, m is not zero and the number of bridging carbons between Z and W is no greater than 5;

W represents hydrogen when T is allylene; or Ar, wherein Ar represents phenyl, 2-, 3- or 4- pyridyl, 2- or 3-thienyl, 2- or 4- imidazolyl, 2-, 3-, 4- or 5- furanyl or X'-, Y'- and Z'- substituted phenyl wherein each of X', Y' and Z' independently is as hereinabove defined for X; and when m is 1 to 3, W represents alkenyl, alkynyl, Z$^1$R$_6$ or Z$^1$COR$_6$ wherein Z$^1$ is O, S, SO, SO$_2$ or NR$_6$;

Y represents —O—, —S—, —SO—, —SO$_2$— or —NR$_6$—;

where in the above definitions:

R$_1$ represents Ar, lower alkyl,

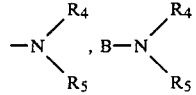

or or Ar-loweralkyl;

R$_4$ and R$_5$ each independently represents hydrogen, lower alkyl, Ar, Ar-lower alkyl, lower alkoxy lower alkyl, trifluoromethyl lower alkyl, or when taken together with the nitrogen atoms to which they are attached represents a 4- to 7-membered cyclic amino or a morpholino group;

R$_6$ represents hydrogen, C$_1$- to C$_{12}$-alkyl, aryl or an arylalkyl group having up to 12 carbon atoms:

R$_7$, R$_7'$ and R$_7''$ each independently represents hydrogen or loweralkyl;

R$_8$ represents hydrogen, lower alkyl, lower alkoxy lower alkyl, trifluoromethyl lower alkyl, Ar-lower alkyl, or Ar;

R$_9$ represents

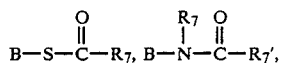

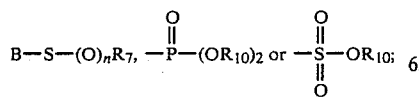

R$_{10}$ represents M, alkali metal or lower alkyl;

R$_{11}$ and R$_{12}$ each independently represents hydrogen or lower alkyl or together represents oxygen;

R$_{13}$ and R$_{14}$ each independently represents hydrogen, alkyl, aryl, or together represents Y;

R$_{15}$ and R$_{16}$ each independently represents hydrogen, alkyl, aryl, or together represent —O— or —S—, provided that when R$_{13}$ and R$_{14}$ together represent —O— or —S—, R$_{15}$ and R$_{16}$ do not represent —O— or —S—;

p and q are each independently 0, 1 or 2 provided that when one of p and q is zero, the other is not zero.

2. A compound of claim 1, in Formula I, wherein R$_2$ and R$_3$ each independently represent —H, —lower alkyl of 1 to 3 carbon atoms, —CH$_2$OH, —CH$_2$CN,

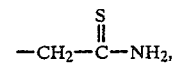

—NH$_2$, —NO or S(O)$_n$—CH$_3$ (wherein n is zero, one or two);

X represents hydrogen;

Z represents —O—, —NH—, —S— or a single bond;

T represents a branched- or straight-chain lower alkylene group;

when Z is a single bond, T also represents an ethenylene or a propenylene group; when Z is —O—, T represents an allylene group; and W represents hydrogen when T is allylene and Z is —O—; and Ar, wherein Ar is selected from substituted-phenyl, phenyl, 2- or 3-thienyl or 2-, 3- or 4-pyridyl groups, wherein there are from one to five-substituents on the phenyl group independently selected from hydrogen, chlorine, fluorine, -t-butyl, —CF$_3$, OCH$_3$, —CN and —OH.

3. A compound of claim 1, in Formula II, wherein R$_2$ and R$_3$ each independently represent —H, —CH$_3$, —CH$_2$OH, —CH$_2$CN,

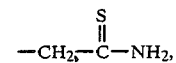

—NH$_2$ or —NO;

X represents hydrogen;

U represents —CH$_2$—O—Ar, wherein Ar is phenyl, o— or p-fluorophenyl, p-chlorophenyl, 2,4,6-trimethylphenyl, 2-thienyl or 3-thienyl.

4. A compound of claim 2 wherein Z—T$_m$—W is in the 8-position and represents phenylmethoxy, phenylmethanamino, thienylmethanamino, phenylethyl, phenylpropyl, thienylethyl, thienylpropyl, 2-phenylethenyl or 3-phenyl-1-propenyl.

5. A compound of claim 3 wherein U is in the 8-position and represents phenoxymethyl.

6. A compound represented by the formula:

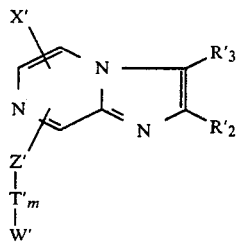

and pharmaceutically acceptable salts thereof, wherein
R'$_2$ and R'$_3$ independently represent methyl, cyanomethyl or amino;
X' represents hydrogen; and
Z'T'$_m$W' represents phenylmethoxy, phenylmethanamino, phenylethyl, 2-phenylethenyl or 3-phenyl-1-propenyl.

7. A compound of claim 6 wherein R'$_2$ and R'$_3$ are each methyl; and Z'T'$_m$W' is phenylmethoxy, i.e. 2,3-dimethyl-8-phenylmethoxyimidazo[1,2-a]pyrazine.

8. The compound of claim 6 wherein R'$_2$ is methyl, R'$_3$ is cyanomethyl and Z'T'$_m$W' is phenylmethoxy, i.e. 2-methyl-8-phenylmethoxyimidazo[1,2-a]pyrazine-3-acetonitrile.

9. The compound of claim 6 wherein R'$_2$ is methyl, R'$_3$ is amino and Z'T'$_m$W' is phenylmethoxy, i.e. 8-phenylmethoxy-2-methyl-3-aminoimidazo[1,2-a]pyrazine.

10. The compound of claim 6 wherein R'$_2$ and R'$_3$ are each methyl and Z'T'$_m$W' is phenylethenyl, i.e. 2,3-dimethyl-8-phenylethenylimidazo[1,2-a]pyrazine.

11. The compound of claim 6 wherein R'$_2$ and R'$_3$ are each methyl and Z'T'$_m$W' is 3-phenyl-1-propenyl, i.e. 2,3-dimethyl-8-(3-phenyl-1-propenyl)imidazo[1,2-a]pyrazine.

12. A method for the treatment of the symptoms of peptic ulcer disease in mammals, which comprises administering to a mammal having peptic ulcer disease a therapeutically effective amount of a compound of claim 1.

13. A method for the treatment of gastric ulcers in mammals which comprises administering to a mammal having gastric ulcers a therapeutically effective amount of a compound of claim 1.

14. A method for the treatment of duodenal ulcers in mammals which comprises administering to a mammal having duodenal ulcers a therapeutically effective amount of a compound of claim 1.

15. A method of inhibiting gastrointestinal irritation and damage in mammals due to administration of drugs which induce gastrointestinal irritation and damage which comprises administering a therapeutically effective amount of a compound of claim 1 during the term said gastrointestional irritating and damaging drug is administered for its therapeutic effect.

16. A method for the treatment of gastrointestinal damage due to stress which comprises administering to a mammal suffering from such damage a therapeutically effective amount of a compound of claim 1.

17. A method for the treatment of the symptoms of peptic ulcer disease in mammals which comprises administering to a mammal having peptic ulcer disease, a therapeutically effective amount of a compound of claims 6, 7, 8, 9, 10 or 11.

18. A pharmaceutical formulation for use in the treatment of ulcers which comprises a compound of claim 1 in a therapeutically effective amount sufficient to alleviate the symptoms of peptic ulcer disease together with a pharmaceutically acceptable carrier.

19. A pharmaceutical formulation for use in the treatment of ulcers which comprises a therapeutically effective amount of a compound of claim 6 sufficient to alleviate the symptoms of peptic ulcer disease together with a pharmaceutically acceptable carrier.

20. A pharmaceutical formulation of claim 19 which comprises a therapeutically effective amount of a compound of claim 7 together with a pharmaceutically acceptable carrier.

21. A pharmaceutical formulation of claim 19 which comprises a therapeutically effective amount of a compound of claim 8 together with a pharmaceutically acceptable carrier.

22. A pharmaceutical formulation of claim 19 which comprises a therapeutically effective amount of a compound of claim 9 together with a pharmaceutically acceptable carrier.

23. A pharmaceutical formulation of claim 19 which comprises a therapeutically effective amount of a compound of claim 10 together with a pharmaceutically acceptable carrier.

24. A pharmaceutical formulation of claim 19 which comprises a therapeutically effective amount of a compound of claim 11 together with a pharmaceutically acceptable carrier.

25. A pharmaceutical composition of claims 18, 19, 20, 21, or 22 suitable for oral administration.

* * * * *